United States Patent [19]

Danon

[11] Patent Number: 5,701,889
[45] Date of Patent: Dec. 30, 1997

[54] OXYGEN BREATHING CONTROLLER HAVING A G-SENSOR

[75] Inventor: Joseph S. Danon, Los Angeles, Calif.

[73] Assignee: Conax Florida Corporation, St. Petersburg, Fla.

[21] Appl. No.: 194,248

[22] Filed: Feb. 10, 1994

Related U.S. Application Data

[63] Continuation-in-part of Ser. No. 929,701, Aug. 12, 1992, Pat. No. 5,348,001.

[51] Int. Cl.[6] ............................................ A63B 9/02
[52] U.S. Cl. ......................... 128/204.29; 128/204.26; 128/205.24
[58] Field of Search ....................... 128/204.29, 204.26, 128/205.24

[56] References Cited

U.S. PATENT DOCUMENTS

| | | | |
|---|---|---|---|
| 3,672,384 | 6/1972 | Hellquist | 128/204.29 |
| 3,752,175 | 8/1973 | Hamilton et al. | 128/204.29 |
| 4,219,039 | 8/1980 | Jaggars | 128/1 A |
| 4,227,444 | 10/1980 | Lincicome | 128/204.29 |
| 4,240,419 | 12/1980 | Furlong et al. | 128/204.23 |
| 4,282,870 | 8/1981 | Porlier | 128/204.29 |
| 4,335,735 | 6/1982 | Cramer et al. | 128/204.26 |
| 4,436,090 | 3/1984 | Darling | 128/204.26 |
| 4,638,791 | 1/1987 | Krogh et al. | 128/204.23 |
| 4,651,728 | 3/1987 | Gupta et al. | 128/204.29 |
| 4,827,964 | 5/1989 | Guido et al. | 128/204.21 |
| 4,856,507 | 8/1989 | Ouillon et al. | 128/204.29 |
| 4,858,606 | 8/1989 | Hamlin | 128/204.29 |
| 5,127,896 | 7/1992 | De Gaston | 128/202.11 |
| 5,170,814 | 12/1992 | Crome | 600/20 |
| 5,199,426 | 4/1993 | Aldworth et al. | 128/204.29 |
| 5,247,926 | 9/1993 | Harral | 128/204.29 |
| 5,348,001 | 9/1994 | Danon | 128/205.24 |
| 5,351,682 | 10/1994 | Foote | 128/205.24 |

*Primary Examiner*—Kimberly L. Asher
*Attorney, Agent, or Firm*—Hodgson, Russ, Andrews, Woods & Goodyear LLP

[57] ABSTRACT

The oxygen breathing controller (10) of the present invention provides a two-stage inlet regulator. In addition, the oxygen breathing controller is provided with an aneroid sensor (100) and a G-sensor (80). The G-sensor has at least two diaphragms (92,93) with G-pressure applied to one of them. Pressure control then depends on a ratio between the effective areas of the diaphragms.

18 Claims, 12 Drawing Sheets

OXYGEN BREATHING CONTROLLER HAVING A G-SENSOR

CROSS-REFERENCE

The present application is a continuation-in-part application of application Ser. No. 07/929,701, filed Aug. 12, 1992, now U.S. Pat. No. 5,348,001 entitled "Oxygen Breathing Controls."

FIELD OF THE INVENTION

This invention relates generally to oxygen supply systems, and more particularly to oxygen breathing controllers which perform precision control over the oxygen supply.

For sophisticated aircraft maneuvers, advanced protection for crew members is necessary. When crew members fly under G-forces, they may suffer blackouts caused by retreating blood which empties away from the face and the upper body. These blackouts are dangerous because the aircraft is flying at a high speed. Even a blackout lasting a few seconds could have a serious consequence. To prevent blackouts, a crew member wears a gravity suit connected to a G-force pressure sensitive valve which pressurizes the G-suit automatically when necessary. This prevents the blood from further retreating to trigger a blackout.

A G-sensor is provided to control the pressures produced by the G-valve during high G maneuvers by the aircraft. In the present invention, the G-sensor functions to deamplify the G-valve pressure.

SUMMARY OF THE INVENTION

The oxygen breathing controller having a G-sensor according to the present invention supplies oxygen to the crew member on schedules which are a function of altitude and G-forces. The oxygen breathing controller supplies positive pressure breathing oxygen from both an on-board oxygen generating system and a liquid oxygen system as required. In addition, the oxygen breathing controller provides pressurization of an upper counterpressure garment at a positive pressure breathing pressure.

At a cabin altitude of up to about 34,000 feet, the oxygen breathing controller supplies 100% oxygen at a positive pressure of approximately 1.0 inches of water. At approximately 34,000 feet to about 50,000 feet of cabin altitude, the oxygen breathing controller supplies oxygen at positive pressures of approximately 1.0 inches of water at about 34,000 feet to approximately 20 inches of water at about 50,000 feet. In the event of a G-maneuver that results in the pressure in a G-suit ranging from between about 3.5 to about 11 psig (4 to 9 G's), then the oxygen pressure supplied by the oxygen breathing controller will be from approximately 1.0 inches of water at 4 G's to about 32.0 inches of water at 9 G's. The oxygen breathing controller automatically selects the greater pressure demanded by either the altitude function or the G-function. In addition, there is a connection between the oxygen breathing controller and the upper counter pressure garment worn by the crew member, the upper counterpressure garment being separate and distinct from the G-suit. The oxygen breathing controller pressurizes this garment to the positive pressure level of the oxygen being supplied to the breather.

The G-sensor of the present invention includes dual diaphragms having an intermediate vent chamber. G-pressure is directed to one diaphragm while outlet pressure is directed against the other to thereby provide for deamplification of the G-pressure by means of proportional diaphragm areas. Deamplification is in a ratio of 6.5 to 1. The deamplified pressure is then transmitted to a servo pilot regulator which in turn modulates a second stage valving assembly to provide positive pressure oxygen to the crew member's oxygen mask and counterpressure garment according to either the G-force or altitude schedules.

DETAILED EXPLANATION OF THE INVENTION

Main Body

Figure 1:
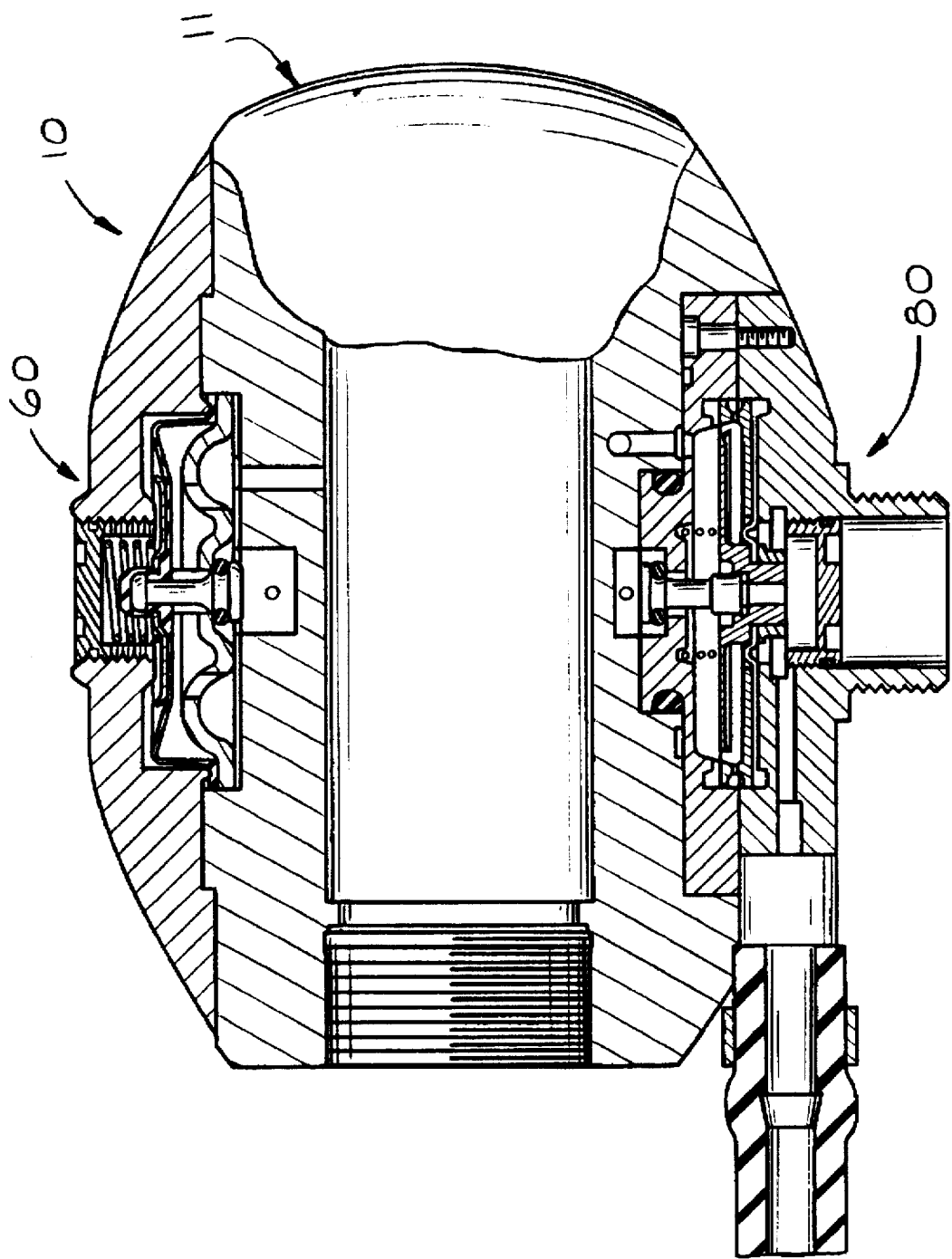
FIG. 1 shows a cross-sectional view of an oxygen breathing controller 10 of the present invention having a servo pilot regulator 60 and a G-sensor assembly 80.
Figure 2:
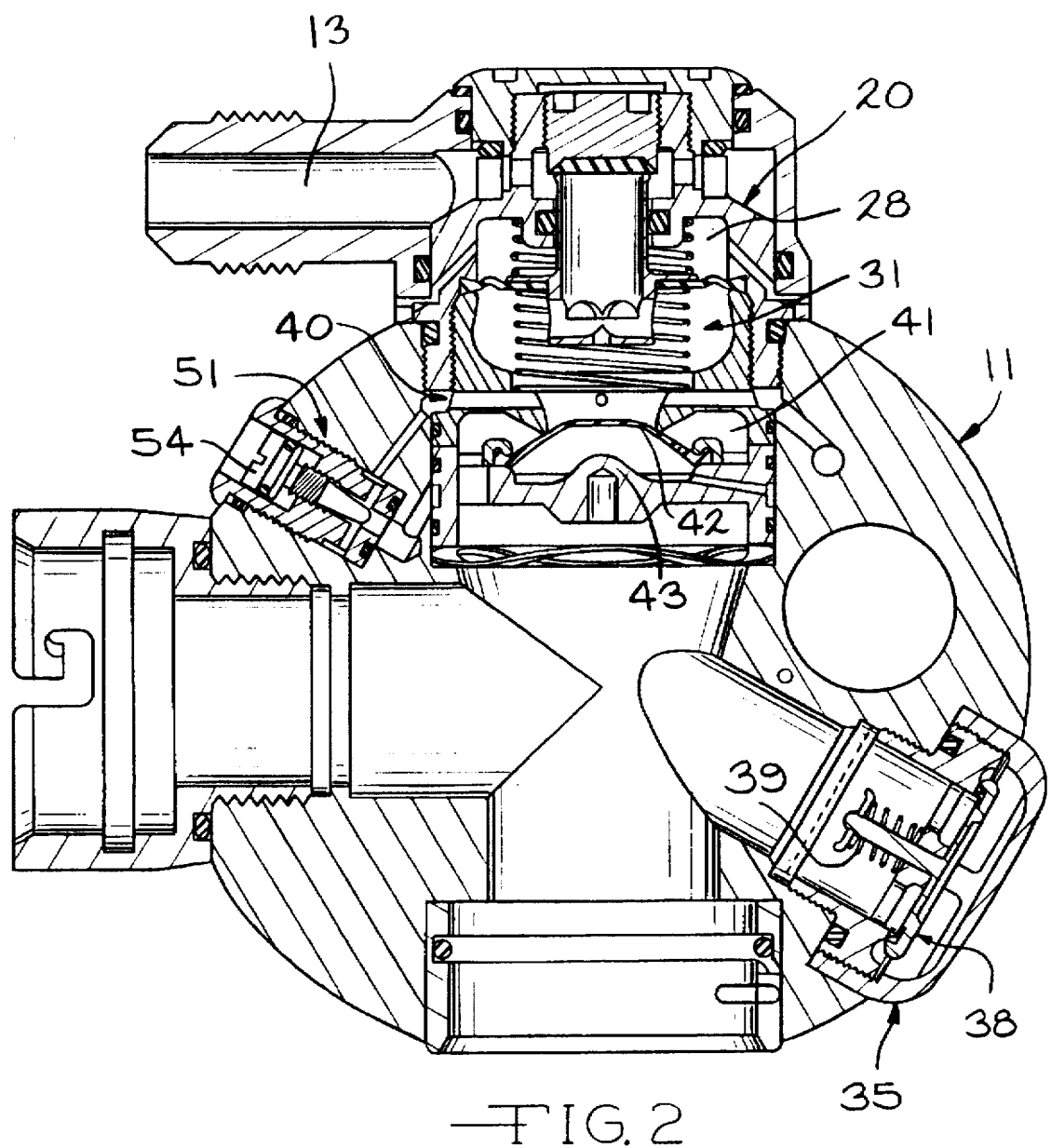
FIG. 2 shows another cross-sectional view of the oxygen breathing controller 10 of the present invention including a first stage regulator assembly 20, a second stage valving assembly 40 and a pressure relief valve 35.

A main body 11 of an oxygen breathing controller 10 according to the present invention is shown in FIGS. 1 and 2 and serves as the main support for all of the components and modules comprising the oxygen breathing controller 10. All connections between the various components and modules for control, primary flow and secondary flow are accomplished internally within the main body 11. The ports are oriented radially to accommodate inlet and outlet connections and various modules that either plug in or fasten to the main body 11.

First Stage Regulator

Figure 3:
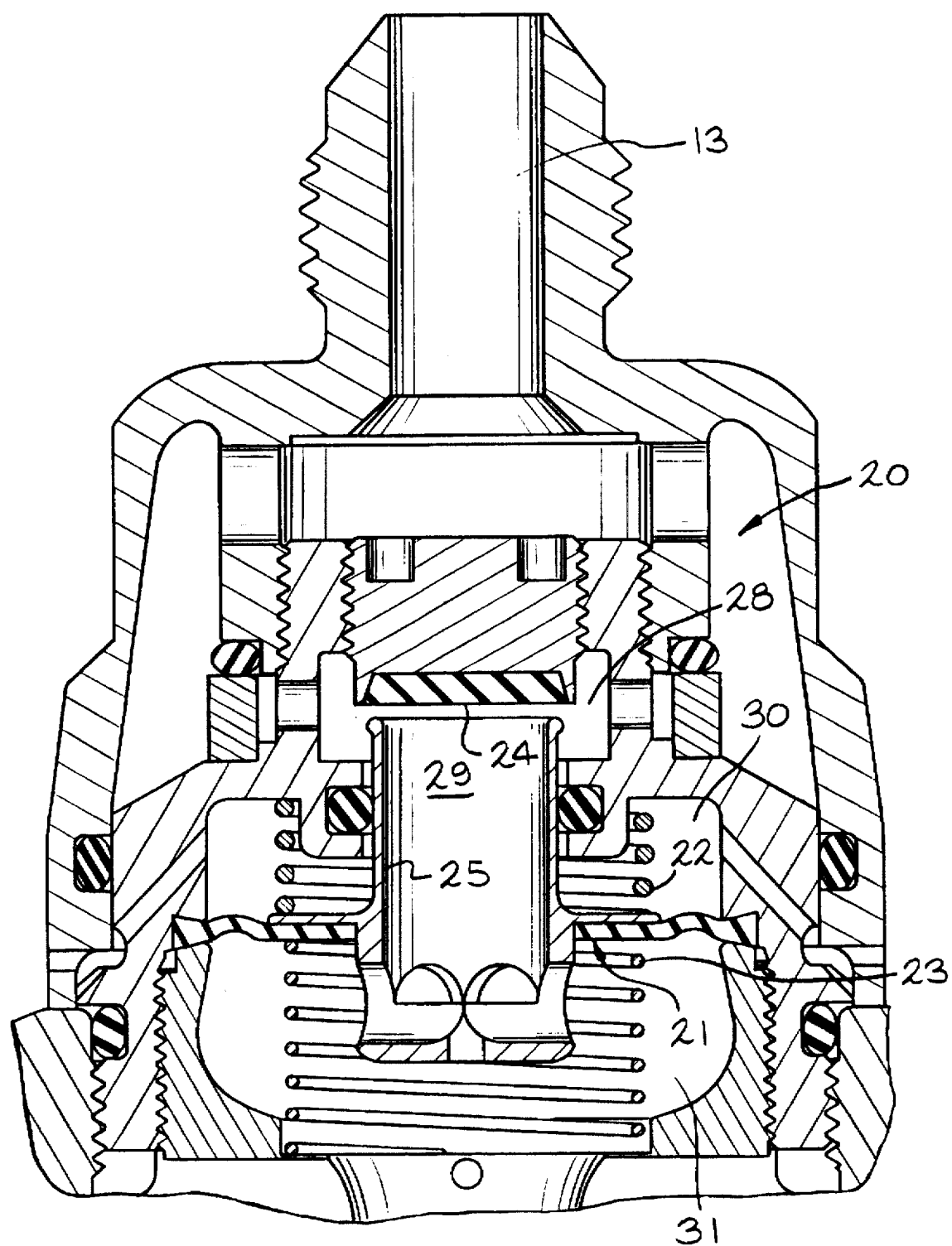
FIG. 3 shows an enlarged, cross-sectional view of the first stage regulator assembly 20.
Figure 7:
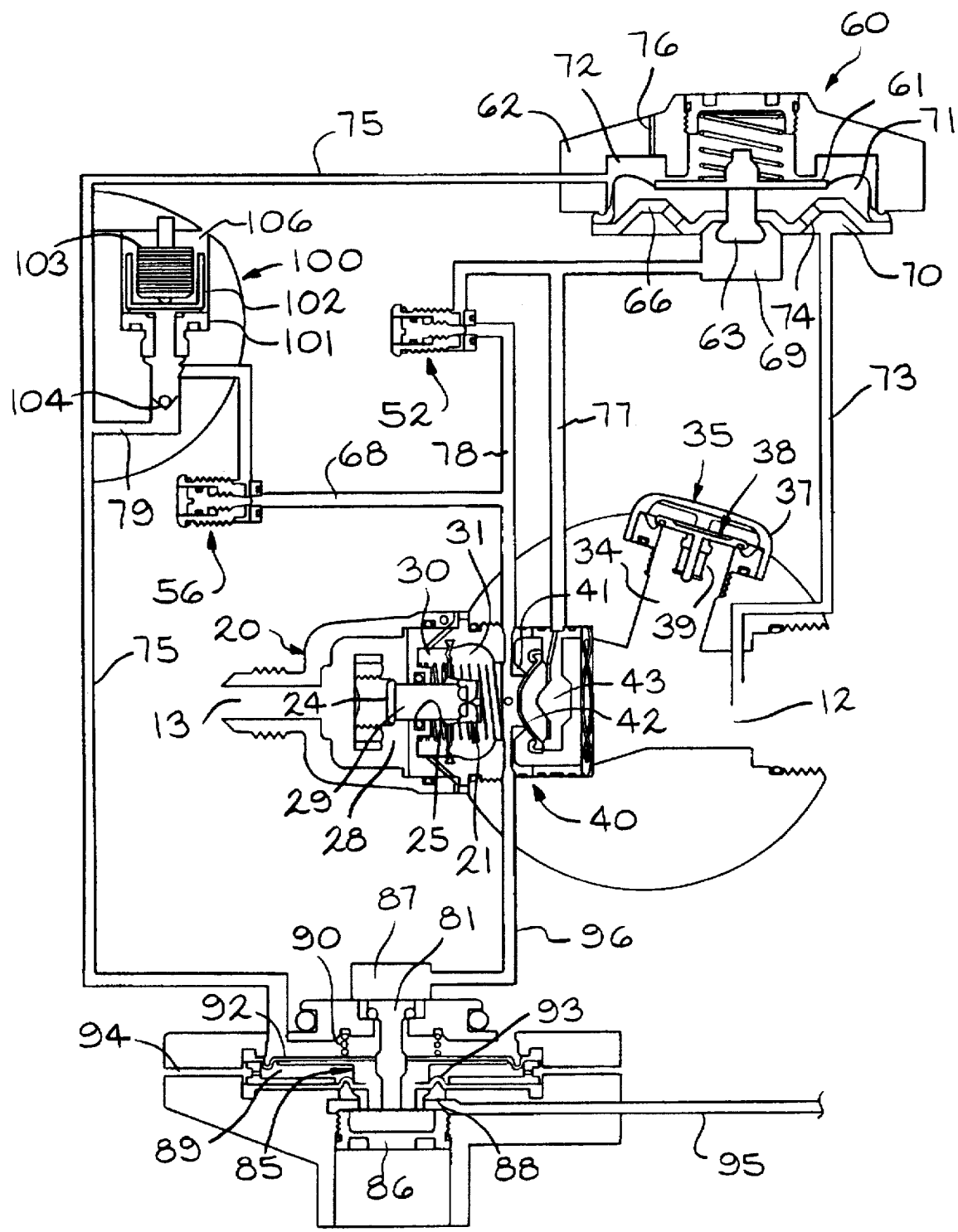
FIG. 7 shows a schematic view of the oxygen breathing controller 10 of the present invention.

A first stage regulator 20 of the oxygen breathing controller 10 is shown in FIGS. 2, 3 and 7. The first stage regulator 20 serves to regulate the oxygen pressure from an inlet pressure of 120 psig to a nominal 5 psig in a single stage. The oxygen flow is received from an inlet 13 to the oxygen breathing controller 10 and is discharged to a second stage valving assembly also shown in FIGS. 2 and 7.

The first stage regulator 20, shown in an enlarged view in FIG. 3, is in its fully opened position with the inlet pressure, P1, in an inlet chamber 28, equal to zero. With the first stage regulator 20 fully opened, an intermediate chamber 29 on the upstream side of a first stage diaphragm assembly 21 is disposed between springs 22 and 23 and in communication with P1 in the inlet chamber 28. An ambient chamber 30 is vented to ambient pressure, Pamb. The second stage valving assembly 40 is closed at the outlet of the first stage regulator 20 if the discharge pressure, P2, in a discharge chamber 31 is zero. Then, P2 is equal to the inlet pressure, P1, which as previously discussed is zero with the first stage regulator 20 fully opened.

If P1 increases, P2 increases correspondingly since the first stage regulator 20 is open with an inlet tube 25 of the first stage diaphragm assembly 21 lifted off of a first stage seat assembly 24. When the inlet pressure, P1, in the inlet chamber 28 reaches approximately 5 psig, the discharge pressure, P2, in the discharge chamber 31 is also approximately 5 psig. At this point, the position of the first stage diaphragm assembly 21 is essentially balanced with the closing pressure force acting on the downstream side of the first stage diaphragm assembly 21 equal to the opening pressure force. In other words, the closing force, acting on the first stage diaphragm assembly 21, which is calculated as P2 times the area of the discharge chamber 31 side of the diaphragm 21 minus Pamb times the area of the ambient chamber 30 side of the diaphragm 21, is equal to the opening pressure force acting on diaphragm 21, which is calculated as P1 times the cross-sectional area of the inlet tube 25 of the first stage diaphragm assembly 21. However, any further increase in P1 results in a corresponding increase in P2, and the closing force acting on the diaphragm assembly 21 overcomes the opening force. As a result, when the pressure in inlet chamber 28 exceeds approximately 5 psig, the first stage diaphragm assembly 21 moves toward the closed position.

If the second stage valving assembly 40 and the first stage regulator 20 are both closed when a positive pressure, P1, is applied to the inlet 13 of the oxygen breathing controller, then there is no breathing demand. As the crew member begins to inhale and oxygen starts to flow, the pressure P2 in the discharge chamber 31 decreases. As the discharge chamber 31 pressure P2 decreases below the set point of the first stage regulator 20, i.e., below approximately 5 psig, the closing pressure on the first stage diaphragm assembly 21 is upset. This causes the inlet tube 25 to lift off of the seat assembly 24, thereby opening the first stage regulator 20. Oxygen then flows from the inlet chamber 28 through a bore of the first stage diaphragm assembly 21, through the intermediate chamber 29 and into the discharge chamber 31. The flow of oxygen increases the pressure in the discharge chamber 31 until pressure equilibrium is restored on the first stage diaphragm assembly 21 at the approximately 5 psig set point of the first stage regulator 20. In this way, regulation of pressure through the first stage regulator 20 is achieved.

Second Stage Valving Assembly

FIGS. 2 and 7 show the second stage valving assembly 40 at a downstream position with respect to the first stage regulator 20. The second stage valving assembly 40 receives oxygen flow from the first stage regulator 20 at the previously described regulated pressure of approximately 5 psig. The discharge from the second stage valving assembly 40 then flows to the outlet 12 of the oxygen breathing controller. The second stage valving assembly 40 functions in conjunction with the servo pilot regulator 60 shown in FIG. 4 to control the oxygen outlet pressure in outlet 12 according to a G-forces schedule (FIG. 8) and an altitude schedule (FIG. 9).

Figure 8:
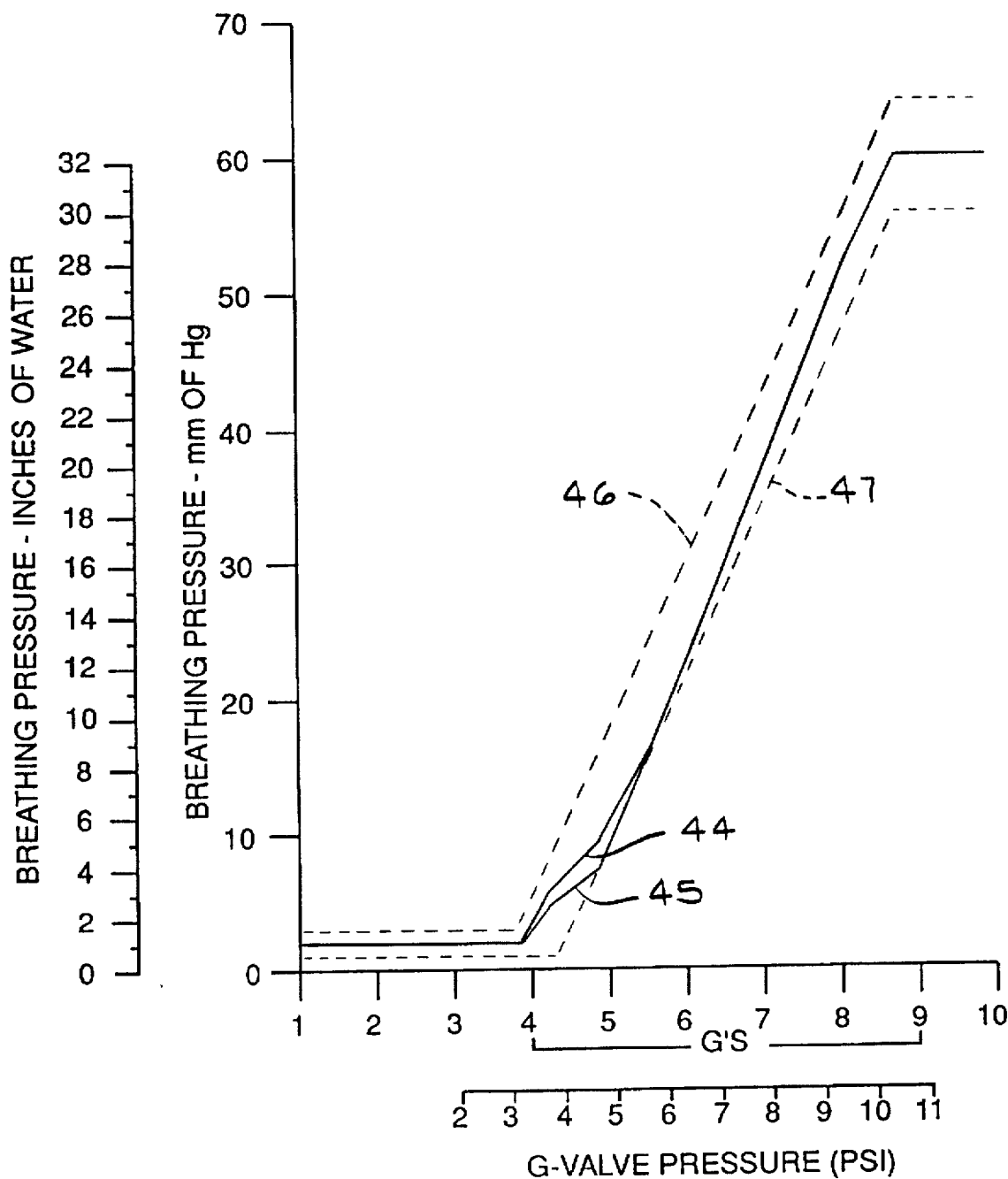
FIG. 8 shows a positive pressure breathing schedule as a function of G-forces.
Figure 9:
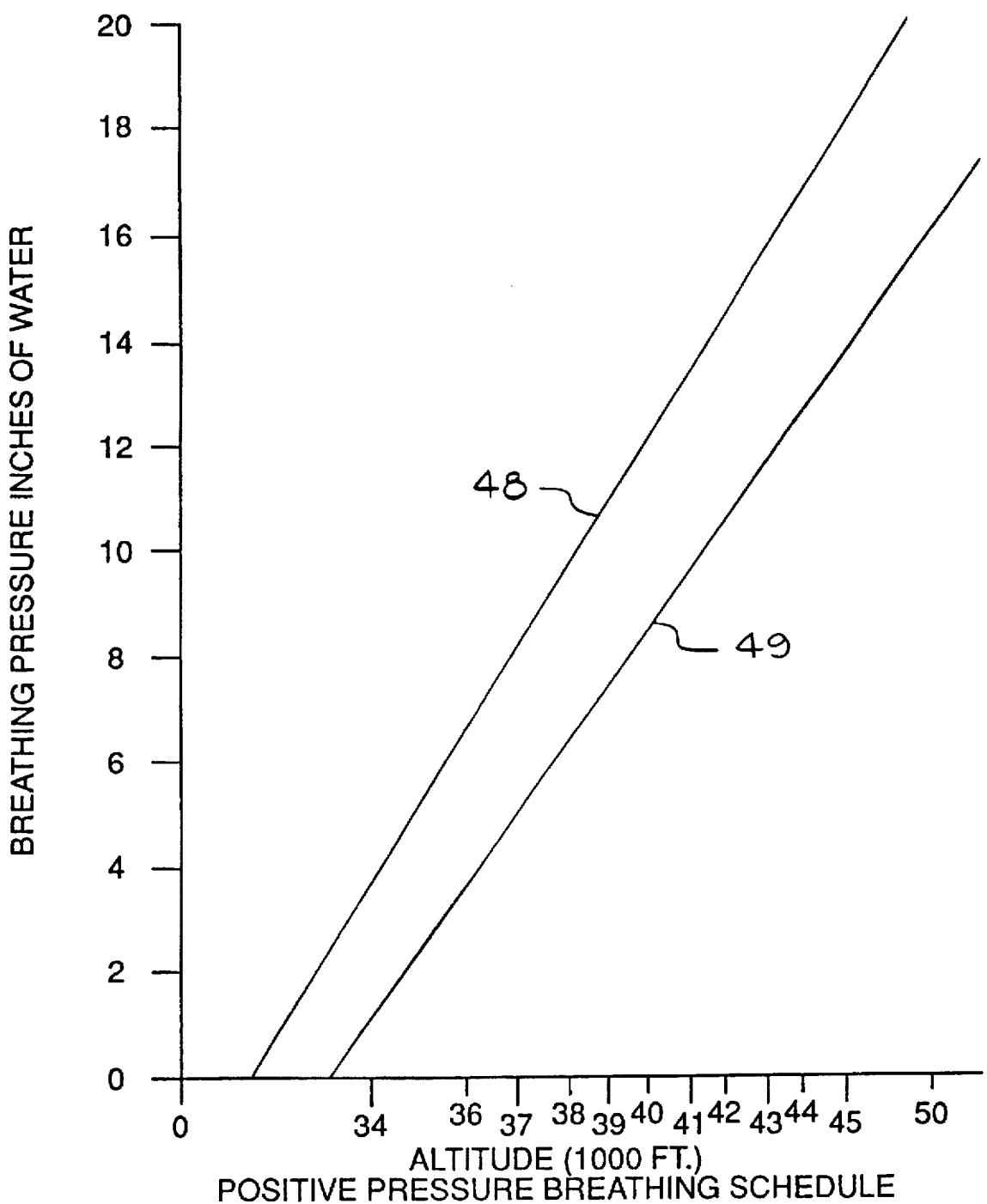
FIG. 9 shows a positive pressure breathing schedule as a function of altitude.

The G-forces schedule shown in FIG. 8 provides positive pressure between about 4 G's to about 9 G's as indicated by curves 44 and 45. The maximum and minimum breathing pressures in the prescribed G-force range are indicated by curves 46 and 47. FIG. 9 shows the maximum and minimum oxygen breathing pressures as a function of altitude between about 34,000 feet and 50,000 feet, as indicated by curves 48 and 49, respectively.

When the second stage valving assembly 40 is in its fully closed, no flow condition, the servo pilot regulator 60 is also closed and the inlet pressure to the servo pilot regulator 60 is equal to a control pressure for this component. In the closed position, the pressures acting on both sides of a second stage diaphragm 42 are equal, and the diaphragm 42 is pressed against a valve seat of a diaphragm cage 41 by its elastic memory. As a result, there is no flow through the second stage valving assembly 40.

If the outlet pressure of the second stage valving assembly 40 decreases to below the pressure set point of the servo pilot regulator 60, the control pressure of the latter component decreases resulting in a pressure difference across the second stage diaphragm 42. This pressure differential causes the diaphragm 42 to lift off of the seat of the diaphragm cage 41, and flow through the second stage valving assembly 40 is initiated. The pressure set point of the servo pilot regulator 60 is approximately 1.5 inches of water at altitudes below approximately 34,000 feet.

When the second stage valving assembly 40 is in its fully opened position, the second stage diaphragm 42 is supported by an outlet housing 43 which prevents stretching and overstress of the diaphragm 42. During normal pressure control, the second stage diaphragm 42 is in an intermediate position (not shown in FIGS. 2 and 7) between the fully closed and the fully opened conditions. The position of the diaphragm 42 is determined by the control pressure of the servo pilot regulator 60 which, as previously discussed, is modulated in response to the G-forces schedule (FIG. 8) and the altitude schedule (FIG. 9).

Servo Pilot Regulator

Figure 4:
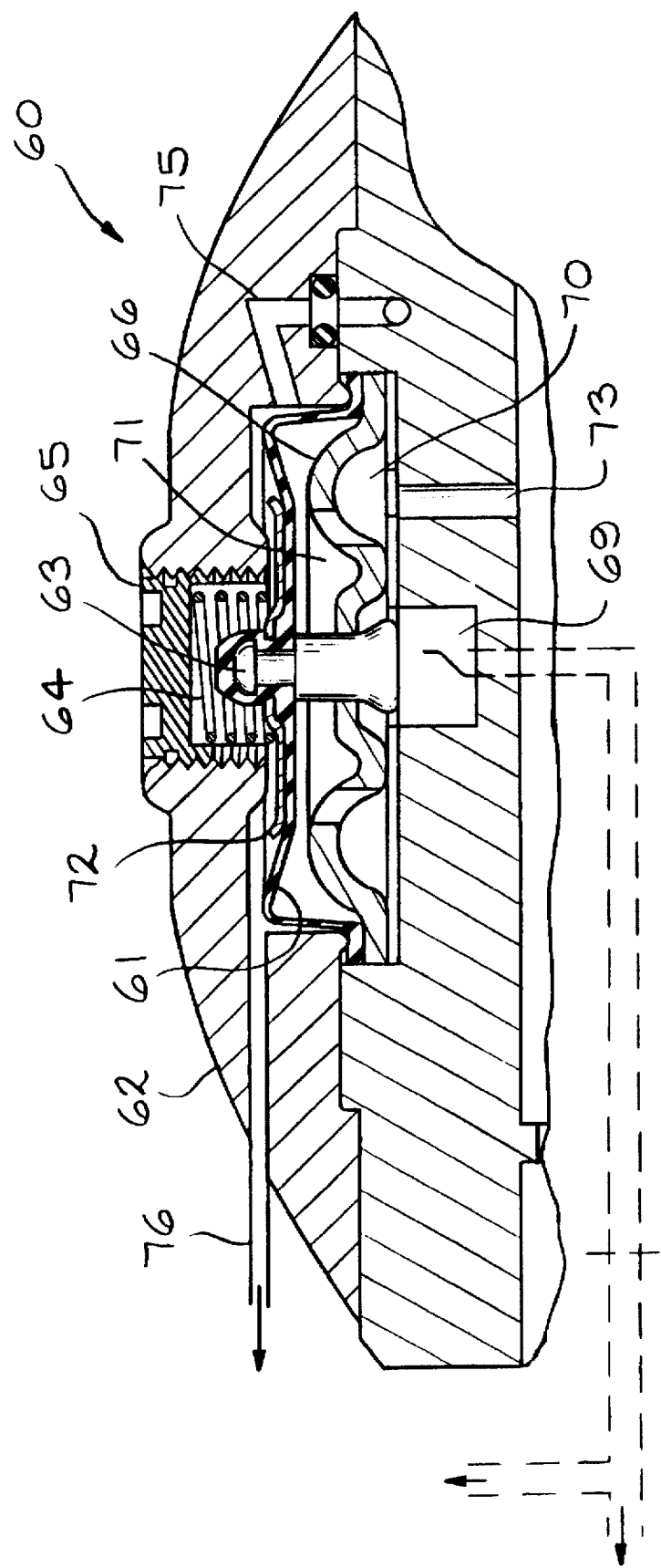
FIG. 4 shows an enlarged, cross-sectional view of the servo pilot regulator 60 shown in FIG. 1.

The servo pilot regulator 60 is shown in FIGS. 1, 4 and 7, and as previously discussed, it provides the control pressure for the second stage valving assembly 40 to regulate the position of the second stage diaphragm 42 so that oxygen flow from the first stage regulator 20 is supplied to the crew member according to the G-forces and altitude schedules. In that manner, the servo pilot regulator 60 responds to signals received from both a G-sensor 80 (FIG. 5) at G-forces of between about 4 G's to 9 G's as a function of the G-forces schedule (FIG. 8) and an aneroid assembly 100 (FIG. 6) at altitudes above approximately 34,000 feet as a function of the altitude schedule (FIG. 9), to control the pressure in the main chamber 12 of the oxygen breathing controller 10 to whichever requirement is the greater as determined be the respective G-forces schedule and the altitude schedule.

The servo pilot regulator 60 is shown in FIG. 4 in its unpressurized configuration having a diaphragm plate assembly 61 biased toward an open position by a spring 64 held by a spring adjustment holder 65. An inlet chamber 69 communicates with the upstream side of the second stage diaphragm 42 of the second stage valving assembly 40 via a port 78 and first flow restrictor 52 to control the pressure behind the second stage diaphragm 42, i.e., in the discharge chamber 31 of the first stage regulator 20. An outlet chamber 70 of the servo pilot regulator 60 communicates via port 73 with a main chamber 12 of the oxygen breathing controller 10 downstream of the second stage valving assembly 40. An intermediate chamber 71, defined partially by an upper pilot cover 62, is connected directly to the servo pilot outlet chamber 70 via holes 74 in a pilot seal plate 66. A vent chamber 72, also defined partially by the upper pilot cover 62, is in communication with the G-sensor 80 and the aneroid assembly 100 via an internal port 75. The vent chamber 72 is also vented to the ambient via a small vent orifice 76.

At ambient altitudes below approximately 34,000 feet and at G-levels below approximately 4 G's, neither the aneroid assembly 100 nor the G-sensor 80 has any effect on the servo pilot regulator 60. As oxygen pressure is communicated to the oxygen breathing controller 10 via the first stage regulator 20 and the second stage valving assembly 40, the servo pilot inlet chamber 69 becomes pressurized and oxygen flows through a poppet pilot 63 into the outlet and intermediate chambers 70 and 71 of the servo pilot regulator 60. From there, the oxygen flows via port 73 to the main chamber 12.

This flow results in a pressure drop through the first flow restrictor 52 which is transmitted as a control pressure to the outlet or downstream side of the diaphragm 42 of the second stage valving assembly 40 via port 77. As previously described, when the outlet pressure of the second stage valving assembly 40 decreases below the pressure set point of the servo pilot regulator 60, a pressure differential is formed across the second stage diaphragm 42, and the diaphragm 42 lifts off of the seat provided by the diaphragm cage 41. Oxygen then flows through the second stage valving assembly 40 and into the main chamber 12 of the oxygen breathing controller 10.

This flow increases the pressure in the main chamber 12 which is sensed by the outlet and intermediate chambers 70 and 71 of the servo pilot regulator 60 via port 73. The pilot poppet 63 then moves towards its closed position (FIGS. 1, 4 and 7) thereby discontinuing flow into the inlet chamber 69. In this way, the pressure in the main chamber 12 of the oxygen breathing controller 10 is regulated to the set point of the servo pilot regulator 60. The pressure in the main chamber 12 reaches approximately 1.5 inches of water at altitudes up to approximately 34,000 feet.

Upon inhalation, the pressure in the main chamber 12 begins to drop. This pressure decrease is sensed by the servo pilot regulator 60 via port 73 to create a pressure imbalance between the outlet and intermediate chambers 70 and 71, and the vent chamber 72 across the diaphragm plate assembly 61 of the servo pilot regulator 60. This pressure imbalance towards the outlet and intermediate chambers 70 and 71 causes the diaphragm plate assembly 61 to deflect towards the area of decreased pressure to open the pilot poppet 63. Flow through the pilot poppet 63 in turn causes the pressure across the first flow restrictor 52 to drop, and again this decreased pressure is communicated to the outlet or downstream side of the diaphragm 42 of the second stage valving assembly 40 via port 77. The diaphragm 42 then lifts off of the diaphragm cage 41 to provide for oxygen flow through the second stage valving assembly 40 to satisfy the breathing demand and to maintain the pressure in the main chamber 12. The breathing demand is satisfied up to about 250 slpm at an inlet pressure of about 50 psig and an outlet pressure of approximately 1.5 inches of water.

As previously discussed, the servo pilot regulator 60 functions in conjunction with the aneroid assembly 100. At ambient altitudes below approximately 34,000 feet, the vent chamber 72 is vented to ambient via port 76, and the aneroid assembly 100 is open with no effect on the servo pilot regulator 60. At approximately 34,000 feet, the aneroid assembly 100 applies sufficient force to an aneroid poppet 102 to prevent flow through the poppet 102, thereby pressurizing the vent chamber 72 in the servo pilot regulator 60. This also causes the pilot poppet 63 to open in response to the oxygen pressure in the vent chamber 72 being greater than that in the outlet and intermediate chambers 70 and 71 of the servo pilot regulator 60. With the pilot poppet 63 open, oxygen flows from the upstream side of the second stage valving assembly 40, i.e., from the discharge chamber 31 of the first stage regulator 20, through the poppet pilot 63 via port 77 and to the main chamber 12 via port 73. This oxygen flow causes a pressure drop through the first flow restrictor 52 which as previously described, is communicated as the control pressure to the outlet of the second stage valving assembly 40 via port 77. The pressure drop through the flow restrictor 52 creates a pressure imbalance across the diaphragm 42 which in turn lifts off of the diaphragm cage 41 to open the second stage valving assembly 40 and provide for oxygen flow to the crew member through the main chamber 12. The servo pilot regulator 60 controls the pressure in the main chamber 12 up to about 50,000 feet where the set point is approximately 20 inches of water.

If G-forces exceed about 4 G's at any altitude, then the G-sensor 80 opens and allows oxygen to pressurize the vent chamber 72 of the servo pilot regulator 60, thereby creating a pressure imbalance across the diaphragm plate assembly 61 to open the poppet pilot 63. The opened poppet pilot 63 allows oxygen to flow from the discharge chamber 31 of the first stage regulator 20 to create a pressure drop through the first flow restrictor 52. The decreased pressure through the first flow restrictor 52 is again communicated as the control pressure to the outlet of the second stage valving assembly 40 via port 77. This causes a pressure imbalance across the diaphragm 42, and the second stage valving assembly 40 opens increasing the oxygen pressure supplied to the crew member. The G-sensor 80 controls at G-forces between about 4 and 9 G's.

G-Sensor

Figure 5:
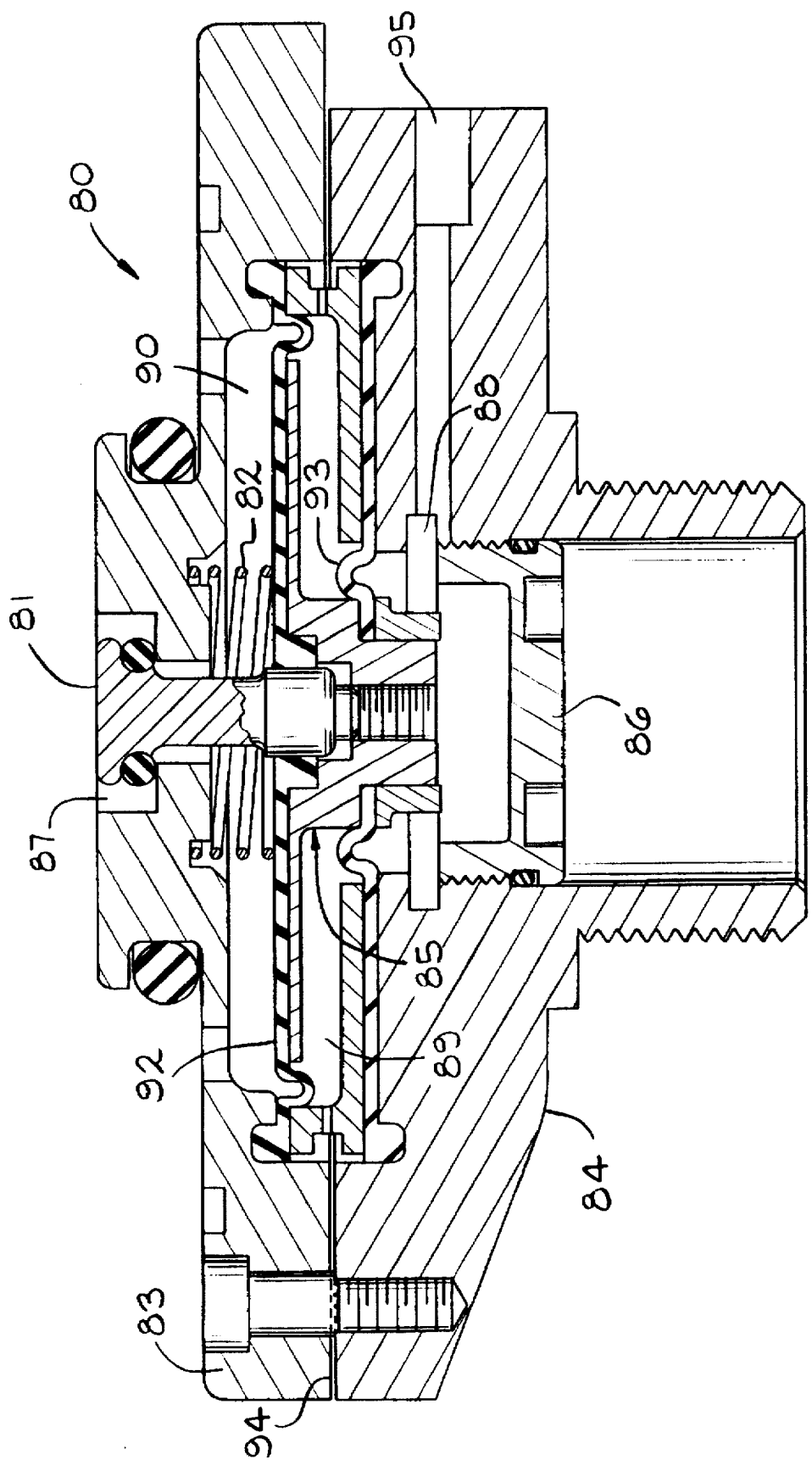
FIG. 5 shows an enlarged, cross-sectional view of the G-sensor assembly 80 shown in FIG. 1.

The G-sensor 80 is shown closed in the enlarged view in FIG. 5 having a poppet 81 centrally disposed in an inner housing 83 and in an outer housing 84. The G-sensor 80 is in the closed position if there is less than about 3.5 psi G-valve pressure (less than about 4 G∝s) acting on the aircraft. A seal cap 86 is also centered in the outer housing 84. The G-sensor 80 responds to pressure readings from a G-valve (not shown) connected to the G-suit worn by the crew member to pressuring the suit and in that way prevents the crew member from blacking out during high aircraft G-maneuvers. Without the pressure from the G-suit, blood in the crew member's head and chest flows toward the lower body during high G-maneuvers, thereby tending to cause the crew member to blackout.

As will be explained in detail presently, the G-sensor 80 provides for deamplification of the G-pressure by means of proportional diaphragm areas rather than external bleed. An ambient chamber 89 of the G-sensor 80 is positioned between an outlet pressure diaphragm 92 and a G-pressure diaphragm 93. The outlet pressure diaphragm 92 and the G-pressure diaphragm 93 support a poppet 81 as an integral unit. These three components are collectively referred to as a diaphragm assembly 85. The ambient chamber 89 is vented to ambient via port 94 while G-valve pressure is directed to the G-pressure diaphragm 93, and outlet pressure is directed to the diaphragm 92. A G-valve chamber 88 formed in part by the G-pressure diaphragm 93 is in pressure communication with the G-valve (not shown) connected to the crew member's G-suit via port 95. Thus, as the G-valve pressure increases to above about 3.5 psi (4 G's), the pressure in the G-valve chamber 88 also increases. An increase in the pressure in the G-valve chamber 88 increases the force on this side of the diaphragm assembly 85 to open the poppet 81. A spring 82 is disposed concentrically with the poppet 81. Since the ambient chamber 89 is vented to ambient via port 94, the ambient chamber 89 does not provide any net force tending to move the diaphragm assembly 85 to either the open or the closed portion. The open position of G-sensor 80 is not shown in either FIGS. 5 or 7.

As the pressure in the G-valve chamber 88 lifts the poppet 81 from its seat, pressure from the discharge chamber 87 is bled into the G-sensor chamber 90 through the seat, thereby increasing the pressure in chamber 90. As shown in FIG. 7, the discharge chamber 87 communicates with the discharge chamber 31 of the first stage regulator 20 via port 96 which, as previously discussed, is regulated to approximately 5 psig. As the pressure in the G-sensor chamber 90 increases, the diaphragm assembly 85 tends to close, thereby decreasing the pressure in the G-sensor chamber 90. This interaction of forces on the diaphragm assembly 85 created by changing pressures in the G-valve chamber 88 and the G-sensor chamber 90 produces a regulated pressure in the G-sensor chamber 90. In that respect, the pressure in the G-sensor chamber 90 is proportional to the ratio of the area of the G-pressure diaphragm 93 exposed to G-valve pressure via port 95 and the area of the outlet pressure diaphragm 92 exposed to the pressure in the chamber 90. In the oxygen breathing controller 10 of the present invention the ratio is 6.5 to 1. Thus, the G-valve pressure is deamplified by the G-sensor 80.

The deamplified pressure leaving the G-sensor 80 is then transmitted to the servo pilot regulator 60 which, as previously described, modulates the second stage valving assembly 40 to provide positive pressure oxygen to the crew member according to the G-forces schedule (FIG. 8). As shown in FIG. 7, a discharge chamber 87 of the G-sensor 80 is connected to the discharge chamber 31 of the first stage regulator 20 via an internal port 96 in the main body 11.

A second G-sensor chamber 90 is connected to the vent chamber 72 in the servo pilot regulator 60 via port 75. As previously described, the servo pilot regulator 60 regulates the outlet pressure of the oxygen breathing controller 10 according to the G-forces schedule (FIG. 8). The vent chamber 72 in the servo pilot regulator 60 is also connected to the aneroid assembly 100 via ports 75 and 79. Hence, the outlet pressure in the main chamber 12 of the oxygen breathing controller 10 is biased by both the G-sensor 80 and the aneroid assembly 100.

Flow Restrictors

The first flow restrictor 52 and a second flow restrictor 56 (FIG. 7) serve as adjustable orifices for the oxygen breathing controller 10. The first flow restrictor 52 is positioned between the second stage valving assembly 40 and the servo pilot regulator 60 while the second flow restrictor 56 is located between the former component and the aneroid assembly 100. An adjustment valve 51 (FIG. 2) of the first flow restrictor 52 has a tapered pin that is moved inwardly and outwardly towards and away from a mating seat 53 by a screw adjustment 54. As the adjustment valve 51 is rotated in a clockwise direction by manipulation of its screw adjustment, the valve 51 moves in an inwardly direction towards the mating seat 53, resulting in a decreased orifice effective area. On the other hand, when the screw adjustment is rotated in a counterclockwise direction, the adjustment valve 51 moves in an outwardly direction away from its seat resulting in an increased effective area. The second flow restrictor 56 functions in a similar manner.

Aneroid Assembly

Figure 6:
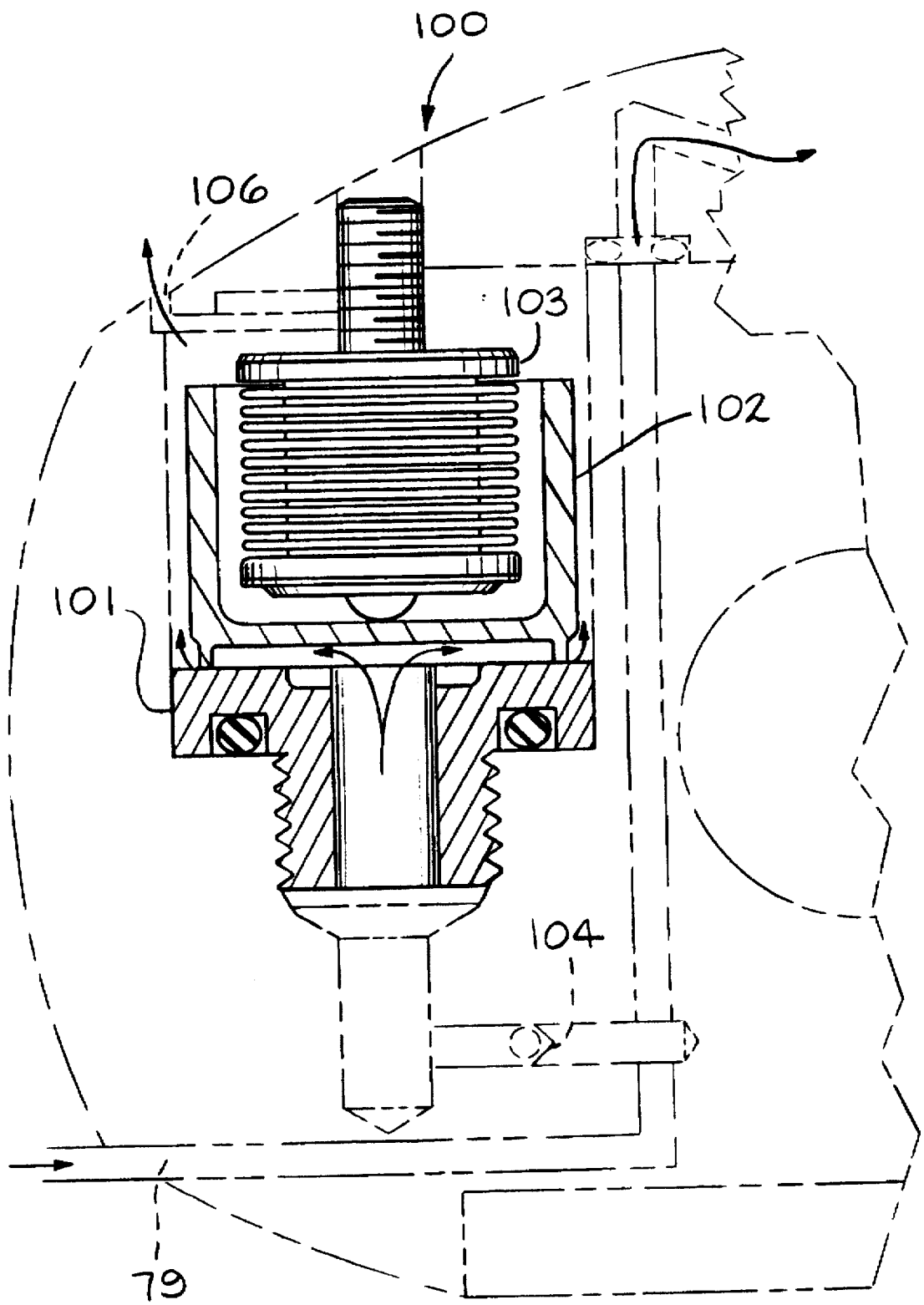
FIG. 6 shows an aneroid assembly 100 of the oxygen breathing controller 10 of the present invention.

The aneroid assembly 100 is shown in FIGS. 6 and 7 and it serves to adjust the breathing schedule of the second stage valving assembly 40 by changing the set point of the servo pilot regulator 60 in response to changes in altitude above about 34,000 feet. Below this altitude, the aneroid assembly 100 allows oxygen to bleed to atmosphere via vent 106. However, as the altitude increases above about 34,000 feet, an aneroid element 103 expands in response to the increased altitude according to the altitude schedule (FIG. 9) resulting in a responsive decrease in the quantity of oxygen being vented to atmosphere. This consequently increases the altitude dependent control pressure to the servo pilot regulator 60 which via ports 75 and 79 in turn controls the oxygen pressure in the main chamber 12 of the oxygen breathing controller 10 above about 34,000 feet according to the altitude schedule. Of course, the servo pilot regulator 60 continues to control the oxygen pressure in the main chamber 12 in response to whichever of the G-forces schedule (FIG. 8) or altitude schedule is greater.

FIG. 6 shows the aneroid assembly 100 closed with the aneroid poppet 102 biased firmly against an aneroid seat 101 by the aneroid element 103. Relative motion between the aneroid poppet 102 and the aneroid seat 101 is effected according to the altitude schedule (FIG. 9). In that manner, the flow of oxygen through the aneroid assembly 100 from its inlet to vent 106 can be thought of as a controlled leak which decreases with altitude, thus effecting the altitude dependent pressure communicated to the servo pilot regulator 60.

The aneroid assembly 100 exerts the minimum force on the aneroid poppet 102 biased towards the aneroid seat 101 at sea level, resulting in the maximum flow or controlled leak at that condition. The second flow restrictor 56 communicating with the inlet flow entering the aneroid assembly 100 via a check valve 104 is adjusted to allow the minimum flow consistent with the altitude schedule. As the altitude increases, the aneroid element 103 expands and exerts increased force on the aneroid poppet 102 biased towards the aneroid seat 101. At an altitude of approximately 34,000 feet, this increased force results in a reduced oxygen flow which in turn increases the control pressure communicated to the servo pilot regulator 60. As previously discussed, the servo pilot regulator 60 controls the pressure in the main chamber 12 of the oxygen breathing controller 10 in response to greater of the G-sensor 80 derived pressure according to the G-forces schedule and the altitude dependent pressure derived from the aneroid assembly 100 according to the altitude schedule. In that respect, the check valve 104 upstream of the aneroid assembly 100 closes when the oxygen pressure from the G-sensor 80 is greater than the oxygen pressure from the aneroid assembly 100. In this manner, the check valve 104 delivers the greater required oxygen pressure to the crew member dependent on either one of the aneroid assembly 100 or the G-sensor 80 that supplies the greater control pressure to the servo pilot regulator 60.

Relief Valve

The preferred embodiment of the oxygen breathing controller 10 of the present invention is further provided with a relief valve 35 (FIGS. 2 and 7) which limits the internal pressure in the main chamber 12 of the oxygen breathing controller to a preset value. As the pressure in the main chamber 12 increases to a value of about 34 inches of water, the opening pressure force acting on a poppet assembly 38 via port 34 overcomes the closing force of a poppet spring 39. The poppet assembly 38 then lifts off of a poppet seat holder 36, thereby opening the relief valve 35 and limiting the pressure in the main chamber 12. The relief valve 35 is held in place by an outlet cap 37.

Functional Description of the Assembly

The operation of the preferred embodiment of the oxygen breathing controller 10 according to the present invention is described herein with reference to FIGS. 7 to 9. FIG. 7 shows a functional schematic of the oxygen breathing controller 10 at sea level with no oxygen pressure being supplied to the inlet 13. Assuming no breathing demand, as oxygen pressure is supplied to the oxygen breathing controller 10, the inlet pressure increases above the approximately 5 psig set point of the first stage regulator 20. The first stage regulator 20 then moves from its static, fully opened position to a fully closed position. Under normal breathing condition, the pressure in the main chamber 12 decreases with each inhalation event and this decreased pressure is sensed by the servo pilot regulator 60 connected to the main chamber 12 by port 73. The communicated pressure decrease causes the pilot poppet 63 of the servo pilot regulator 60 to open, thereby allowing oxygen to flow from the upstream side of the second stage valving assembly 40, i.e., in the discharge chamber 31 of the first stage regulator 20, through the flow restrictor 52 and the pilot poppet 63 and finally to the main chamber 12. Such a flow causes a pressure drop through the flow restrictor 52 which is transmitted as the control pressure to the outlet or downstream side of the diaphragm 42 of the second stage valving assembly via port 77. When the outlet pressure of the second stage valving assembly 40 decreases below the pressure set point of the servo pilot regulator 60, a pressure differential forms across the second stage diaphragm 42, which then opens and allows oxygen flow into the main chamber 12.

Oxygen flow into the main chamber 12 increases the pressure there and reduces the flow through the servo pilot regulator 60. The reduced flow through the servo pilot regulator 60 in turn reduces the pressure drop through the flow restrictor 52 which then reduces the pressure in the discharge chamber 31 of the first stage regulator 20, causing the second stage valving assembly 40 to move towards its closed position (FIG. 2). Closing the second stage valving assembly 40 decreases the pressure in the main chamber 12. In this way, the pressure in the main chamber 12 is controlled according to the pressure set point of the servo pilot regulator 60, which is approximately 1.5 inches of water at altitudes below approximately 34,000 feet.

Below about 34,000 feet and with zero G's acting on the aircraft, the aneroid assembly 100 has no influence on the pressure set point of the servo pilot regulator 60. The oxygen flow to the aneroid assembly 100 therefore passes through the second flow restrictor 56 and is bled to ambient through the vent 106 of the assembly 100. Since there is no G-forces acting on the aircraft, the G-valve pressure will be zero, and the G-sensor 80 will be closed.

Operation Below About 34,000 Feet With About 4 To 9 G's

When G-forces acting on the aircraft are between about 4 G's to 9 G's, the G-sensor 80 influences the operation of the oxygen breathing controller. As shown in the schedule in FIG. 8 of G-forces vs. positive pressure breathing, at approximately 4 G's, the positive pressure breathing schedule requires a breathing pressure of approximately 1.5 inches of water up to approximately 32 inches of water at 9 G's. Thus, during aircraft operation below about 34,000 feet and below about 4 G's, the oxygen breathing controller 10 supplies oxygen to the main chamber 12 at approximately 1.5 inches of water at the demanded breathing rate. If the G-forces increase to above about 4 G's, then the G-valve pressure is increased to above about 3.5 psig as shown in FIG. 8. The diaphragm assembly 85 of the G-sensor 80 forces open the poppet 81, and oxygen flows through the G-sensor 80 to the aneroid assembly 100 via ports 75 and 79. Since the aneroid poppet 102 is not biased firmly against the aneroid seat 101 at altitudes below about 34,000 feet, the oxygen flow through the aneroid assembly 100 is bled through the aneroid seat 101 to ambient via vent 106. When the pressure acting on the check valve 104 is greater on the G-sensor 80 side than on the aneroid assembly 100 side, and the check valve 104 actuates to transmit the pressure of the G-sensor 80 to the servo pilot regulator 60 via port 75 in the main body 11 and to close off transmission of pressure from the aneroid assembly 100 to the servo pilot regulator 60.

The pressure of the G-sensor 80 influences the servo pilot regulator 60 to cause the pilot poppet 63 to open and admit oxygen flow to the main chamber 12. This causes a pressure drop in the flow restrictor 52 to decrease the pressure in the discharge chamber 31 of the first stage regulator 20 and behind the second stage diaphragm 42, thereby causing the second stage valving assembly 40 to open. This in turn increases the pressure in the main chamber 12 according to the G-forces schedule shown in FIG. 8.

Altitude Operation With Zero G'S

As shown in FIG. 9, at an altitude of approximately 34,000 feet, the oxygen breathing controller 10 according to the present invention supplies positive pressure oxygen to the breather at approximately 1.0 inches of water. At higher altitudes, the aneroid element 103 expands and biases the aneroid poppet 102 towards the aneroid seat 101 to reduce the flow therethrough. This results in an increase in the pressure transmitted to the diaphragm plate assembly 61, via ports 78, 68, 79, and 75 communicating from the discharge chamber 31 of the first stage regulator 20 to bias the servo pilot regulator 60 to open. In this way, the servo pilot regulator 60 responds by supplying oxygen at a greater pressure as the altitude increases. At about 50,000 feet, the positive pressure breathing is approximately 20 inches of water.

Altitude Operation With 4 To 9 G'S

As previously discussed, the oxygen breathing controller 10 of the present invention supplies positive pressure oxygen to the crew member according to either a G-force dependent schedule (FIG. 8) or an altitude dependent schedule (FIG. 9). The controlling schedule is determined by which ever of the G-sensor 80 or aneroid assembly 100 requires the greater oxygen pressure due to the aircraft conditions. At altitudes below approximately 34,000 feet and with less than about 4 G's, oxygen is supplied at approximately 1.5 inches of water as stated above. At approximately 34,000 feet, the aneroid element 103 exerts enough force on the aneroid poppet 102 to reduce the oxygen flow between this member and the aneroid seat 101. This results in an increase in the pressure acting on the diaphragm plate assembly 61 via ports 78, 68, 79 and 75 communicating from the discharge chamber 31 of the first stage regulator 20 to bias the servo pilot regulator 60 to an open position. In this manner, oxygen is supplied at a greater pressure as the altitude increases according to the altitude schedule (FIG. 9).

When the G-forces acting on the aircraft are between about 4 to 9 G's at altitude of less than approximately 34,000 feet, the operation of the oxygen breathing controller is as described above. As the altitude increases to above about 34,000 feet and with the G-forces between about 4 and 9 G's, the G-sensor 80 and the aneroid assembly 100 compete for control of the oxygen pressure delivered to the servo pilot regulator 60 to in turn regulate the second stage valving assembly 40. As previously described, whichever of the G-sensor 80 or aneroid assembly 100 that demands the greater oxygen pressure is the one that dictates the magnitude of the positive oxygen pressure delivered to the main chamber 12 via the second stage valving assembly 40.

In that manner, when both the G-sensor 80 and the aneroid assembly 100 dictate that oxygen must be supplied to the crew member at a positive position, control range differentiation provided by the check valve 104 occurs to select the proper positive pressure breathing schedule for a given condition. Thus, if the altitude is above approximately 34,000 feet, the aneroid assembly 100 produces an oxygen pressure signal proportional to the altitude as shown in FIG. 9. On the other hand, if the G-forces are between about 4 and 9 G's, the G-sensor 80 produces an oxygen pressure signal proportional to the G-level as shown in FIG. 8. The oxygen pressure signals produced by the G-sensor 80 and the aneroid assembly 100 are both applied to the check valve 104, and the greater of the two pressure signals is transmitted to the servo pilot regulator 60 to admit oxygen flow to the main chamber 12 in conjunction with regulating flow through the second stage valving assembly 40, as previously described in detail.

Overpressure Relief

The relief valve 35 shown in FIGS. 2 and 7 provides overpressure protection for the crew member's lungs at all altitudes. In the event that the second stage valving assembly 40 malfunctions, venting of pressure in the main chamber 12 is provided by the relief valve 35. The relief valve 35 starts to open at an internal pressure of about 32 inches of water and fully opens at about 36 inches of water with a flow capacity of about 250 slpm.

Servo Pilot Regulator Embodiments

Figure 10:
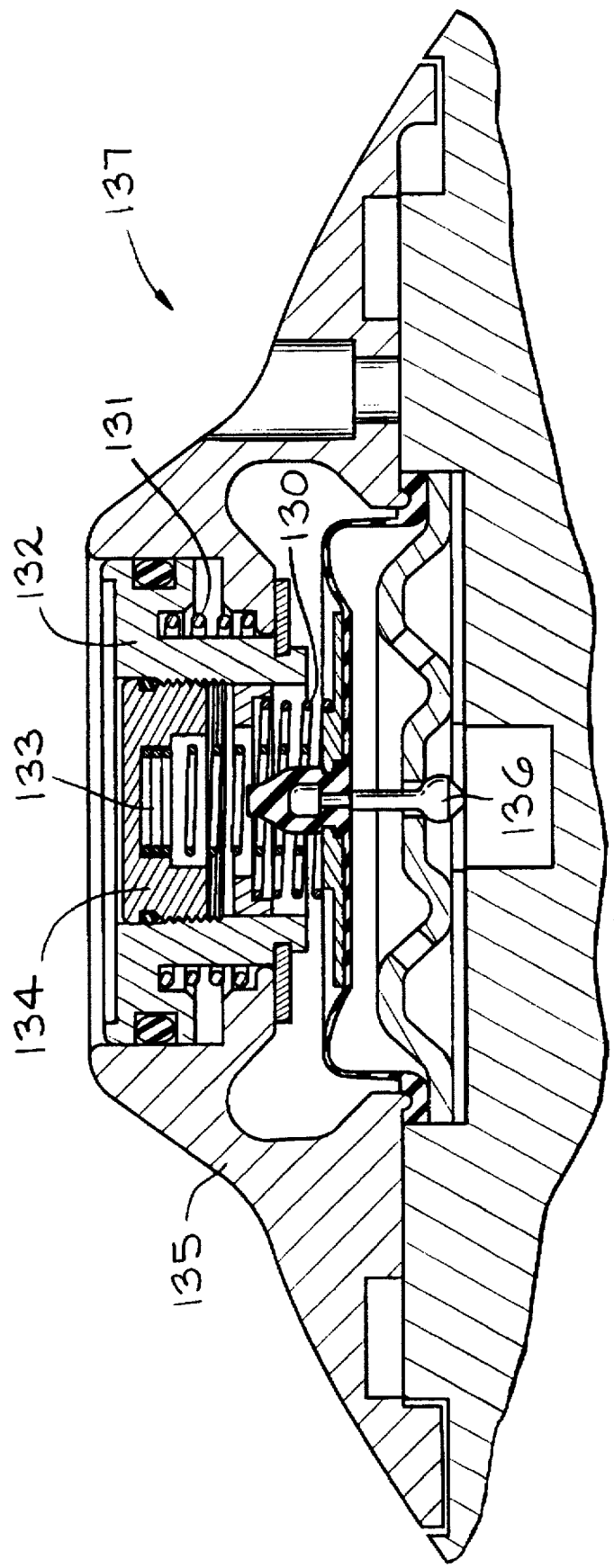
FIG. 10 shows a cross-sectional view of another embodiment of a servo pilot regulator 137 that is useful as a component in the oxygen breathing controller 10 of the present invention.

FIG. 10 shows another embodiment of a servo pilot regulator 137 according to the present invention having a regulator cover 135 housing a regulator spring 130, a return spring 131 that serves to bias a release button 132, a second spring 133, and an adjustment 134 which abuts the second spring 133. The release button 132 abuts a poppet 136 when depressed to provide for fluid flow therethrough.

Figure 11:
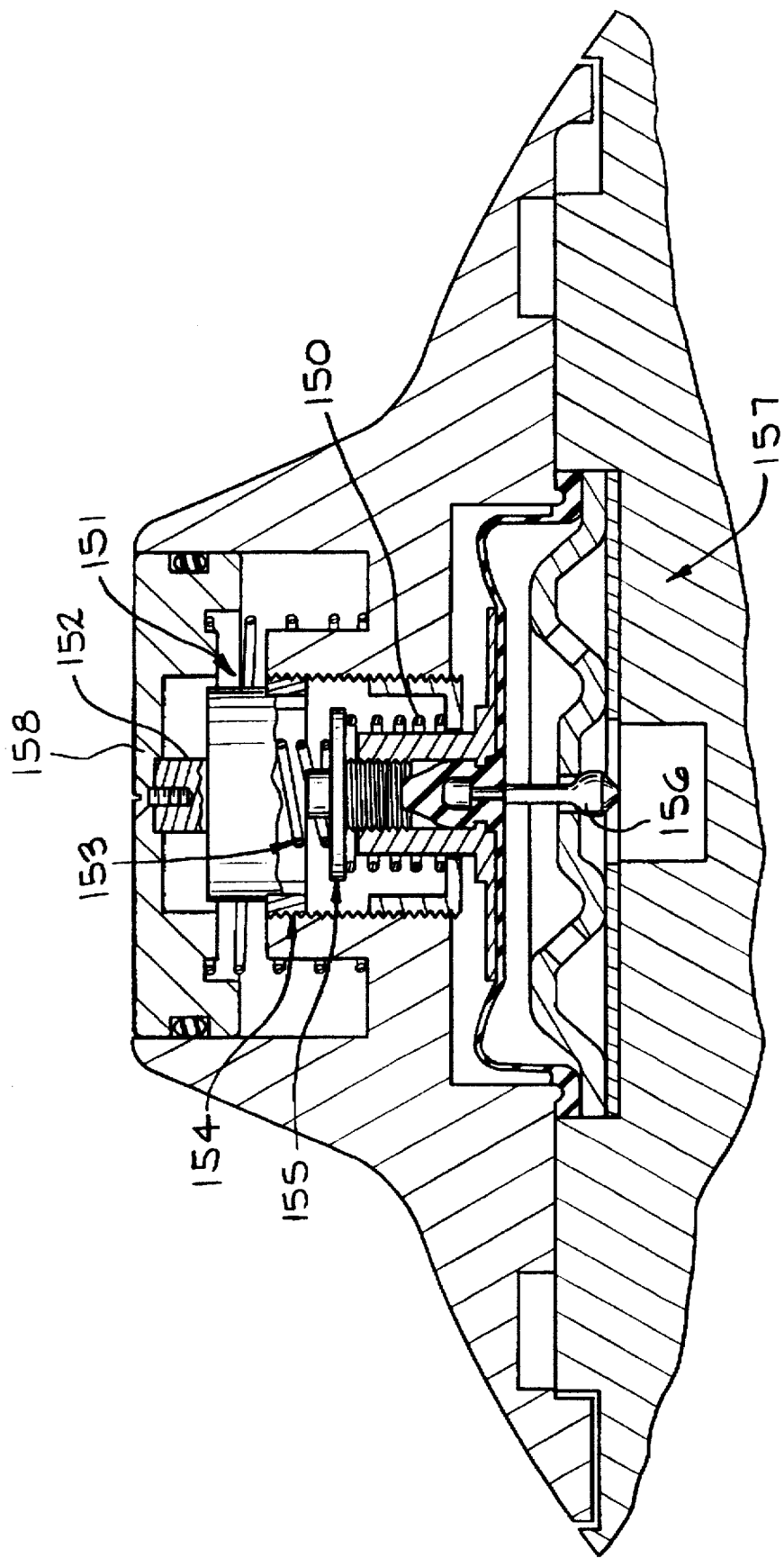
FIG. 11 shows a cross-sectional view of yet another embodiment of a servo pilot regulator 157.
Figure 12:
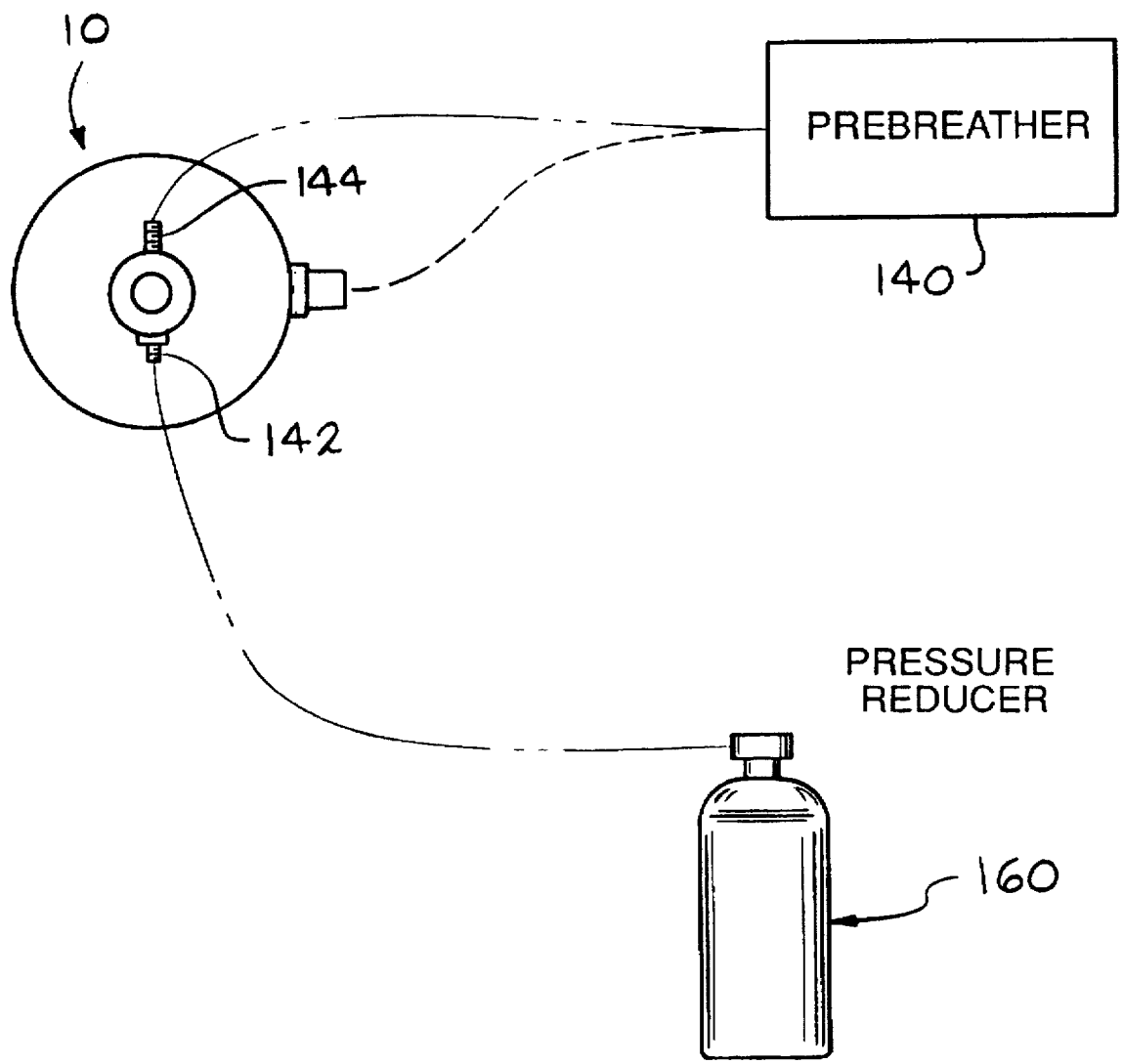
FIG. 12 shows a schematic diagram of the oxygen breathing controller connected to a personal oxygen supply 160.

FIG. 11 shows yet another embodiment of a servo pilot regulator 157 employing a housing 151, a button 158, a poppet 156, a regulator spring 150, a plunger 152, another spring 153 and an adjustment 154 for the spring 153. An outlet pressure regulator spring adjustment 155 is provided between the springs 150 and 153. FIG. 12 shows a regulator hook-up with a prebreather 140 and a personal oxygen supply 160.

Either of the servo pilot regulators 137 and 157 may be used in place of the servo pilot regulator 60. For example, the servo pilot regulator 137 can delivers 14" WC pressure to the mask when the button 132 is depressed. The pressurized flow allows the user to determine if a leak exists between the mask and the user's face. The button 132 returns to the original position once it is released.

The servo pilot regulator 157 is employed on the regulator first stage swivel head having two inlet pressure connections 142 and 144. One inlet is connected to a personal oxygen bottle 160, and the other is connected to the prebreather 140. During prebreathing, the parachutists depresses the button 158 which pushes the servo pilot poppet 156 to allow breathing of 100% oxygen from the prebreather container 140. The bottom 158 remains depressed until the user depresses it again to return it to the original position, thereby switching to the personal oxygen supply 160. This structure eliminates one of the breathing regulators, i.e., regulators 20, 60 in FIGS. 3, 4 and 7, between the prebreathing console and breathing regulator worn by the user.

Having described the preferred embodiment of the oxygen breathing controller, according to the present invention, it should be apparent that various additional objects and advantages have been attained by the present invention and that a variety of modifications can be made within the scope and spirit of the present invention.

What is claimed is:

1. An oxygen breathing controller for supplying an oxygen containing fluid to a user, which comprises:
  a) a first stage regulator means provided to regulate a pressure of the oxygen containing fluid from a source pressure to a reduced, set point pressure that is somewhat greater than an inhalation pressure suitable for inhalation by the user, the first stage regulator means comprising:
    i) a first stage inlet chamber for receiving the oxygen containing fluid at the source pressure; and
    ii) a first stage outlet chamber for providing the oxygen containing fluid at the set point pressure, wherein when the pressure in the first stage outlet chamber is at the set point pressure, fluid flow communication between the first stage inlet chamber and the first stage outlet chamber is closed, and wherein when the pressure in the first stage outlet chamber is below the set point pressure, fluid flow communication between the first stage inlet and outlet chambers is present to raise the pressure in the first stage outlet chamber back to the set point pressure; and
  b) a second stage regulator means in fluid flow communication with the first stage regulator means and disposed downstream thereof, the second stage regulator means comprising:
    i) a second stage inlet chamber in fluid flow communication with the first stage outlet chamber;
    ii) a second stage outlet chamber disposed downstream of the second stage inlet chamber and leading to a breathing apparatus for supplying the user's breathing requirements;
    iii) a diaphragm means separating the second stage inlet chamber and the second stage outlet chamber; and
    iv) means for selectively creating a pressure differential across the second stage inlet chamber and the second stage outlet chamber for flexing the diaphragm means between a closed, no flow position and an open, flow position to provide the breathable oxygen containing fluid to the user upon the occurrence of an inhalation event, wherein with an altitude below an altitude threshold and a G-force below a G-force threshold and upon the occurrence of the inhalation event, the diaphragm means is in the open, flow position with the inhalation pressure transmitted to the second stage inlet chamber to thereby cause the pressure in the first stage outlet chamber to fall below the set point pressure so that fluid flow communication between the first stage inlet and outlet chambers is present to admit additional oxygen containing fluid into the first stage outlet chamber to thereby raise the pressure therein back to the set point pressure to close off communication between the first stage inlet chamber at the source pressure and the first stage outlet chamber at the set point pressure while fulfilling the user's breathing requirements, and wherein when the user's breathing requirements increase due to an increase in either the altitude above the altitude threshold or an increase in the G-forces above the G-force threshold or both, the means for selectively creating the pressure differential across the second stage inlet chamber and the second stage outlet chamber of the second stage regulator means flexes the diaphragm means between the closed, no flow position and the open, flow position at an increased pressure differential in response to the greater of an altitude dependent breathing requirement and a G-force dependent breathing requirement, respectively.

2. The breathing controller of claim 1 wherein the means for selectively creating the pressure differential across the second stage inlet chamber and the second stage outlet chamber of the second stage regulator means includes a G-force sensor means in fluid flow communication with the second stage regulator means and comprising a first G-sensor diaphragm means having a first effective area and a second G-sensor diaphragm means having a second effective area, the first and second effective areas having a predetermined ratio.

3. The oxygen breathing controller of claim 2 wherein the second G-sensor diaphragm means is exposed to a pressure of the a G-valve.

4. The oxygen breathing controller of claim 2 wherein the G-force sensor means includes an atmospheric chamber vented to atmosphere and disposed between the first and second G-sensor diaphragm means.

5. The oxygen breathing controller of claim 2 wherein the predetermined ratio of the first and second effective areas is substantially 6.5 to 1.

6. The oxygen breathing controller of claim 1 further comprising means for shutting the fluid flow during exhalation.

7. The oxygen breathing controller of claim 1 further comprising a flow restrictor means for restricting the fluid flow between the second stage inlet chamber and the second stage outlet chamber of the second stage regulator means.

8. The breathing controller of claim 1 wherein the means for selectively creating the pressure differential includes an aneroid means which regulates the pressure differential across the second stage inlet chamber and the second stage outlet chamber of the second stage regulator means based on altitude, and wherein when the altitude is above the altitude threshold, the higher the altitude, the greater the pressure differential to thereby flex the diaphragm means towards the open position.

9. The breathing controller of claim 1 wherein the means for selectively creating the pressure differential across the second stage inlet chamber and the second stage outlet chamber of the second stage regulator means includes an aneroid means in fluid flow communication with the second regulator means, the aneroid means comprising an aneroid chamber defining a flow opening in one wall and a vent opening in another wall; a bleed stem disposed in the flow opening; and a control aneroid disposed in the aneroid chamber, wherein when the altitude is below the altitude threshold, a portion of the oxygen containing fluid in the second stage inlet chamber flows through the vent opening, and wherein in response to an increase in altitude above the altitude threshold, the control aneroid expands and displaces the bleed stem in the flow opening to thereby permit the oxygen containing fluid to flow between the second stage inlet chamber and the second stage outlet chamber to increase the pressure differential across the second stage regulator means, and wherein when the altitude is above the altitude threshold, the higher the altitude, the greater the pressure differential to thereby flex the diaphragm means towards the open position.

10. A method for regulating an oxygen containing fluid flow to a breathing mask worn by a user in an aircraft during flight, comprising the steps of:

a) controlling an intake of the fluid into the breathing mask in two stages comprising:
   providing a first stage regulator means for regulating a pressure of the oxygen containing fluid from a source pressure to a reduced, set point pressure that is somewhat greater than an inhalation pressure suitable for inhalation by the user, and a second stage regulator means in fluid flow communication with the first stage regulator means and disposed downstream thereof, the first stage regulator means comprising:
   i) a first stage inlet chamber for receiving the oxygen containing fluid at the source pressure; and
   ii) a first stage outlet chamber for providing the oxygen containing fluid at the set point pressure wherein when the pressure in the first stage outlet chamber is at the set point pressure, fluid flow communication between the first stage inlet chamber and the first stage outlet chamber is closed, and wherein when the pressure in the first stage outlet chamber is below the set point pressure, fluid flow communication between the first stage inlet and outlet chambers is present to raise the pressure in the first stage outlet chamber back to the set point pressure; and
   providing a second stage regulator means comprising:
   i) a second stage inlet chamber in fluid flow communication with the first stage outlet chamber;
   ii) a second stage outlet chamber disposed downstream of the second stage inlet chamber and leading to a breathing apparatus for supplying the user's breathing requirements;
   iii) a diaphragm means separating the second stage inlet chamber and the second stage outlet chamber;

b) selectively creating a pressure differential across the second stage inlet chamber and the second stage outlet chamber for flexing the diaphragm means between a closed, no flow position and an open, flow position thereby providing the breathable oxygen containing fluid to the user upon the occurrence of an inhalation event, wherein with an altitude below an altitude threshold, a G-force below a G-force threshold and upon the occurrence of the inhalation event, and with the diaphragm means residing in the open, flow position, the inhalation pressure is transmitted to the second stage inlet chamber thereby causing the pressure in the first stage outlet chamber to fall below the set point pressure with fluid flow communicating between the first stage inlet and outlet chambers and admitting additional oxygen containing fluid into the first stage outlet chamber at the set point pressure while fulfilling the user's breathing requirements, and c) including selectively increasing the pressure differential required to flex the diaphragm means between the closed, no flow position and the open, flow position when the user's breathing requirements increase due to an increase in either the altitude above the altitude threshold or an increase in the G-forces above the G-force threshold or both, the increased pressure differential for flexing the diaphragm means being the greater of an altitude dependent breathing requirement and a G-force dependent breathing requirement.

11. An oxygen breathing controller for supplying an oxygen containing fluid to a user, which comprises:

a) a first stage regulator means provided to regulate a pressure of the oxygen containing fluid from a source pressure to a reduced, set point pressure that is somewhat greater than an inhalation pressure suitable for inhalation by the user, the first stage regulator means comprising:

i) a first stage inlet chamber for receiving the oxygen containing fluid at the source pressure; and ii) a first stage outlet chamber for providing the oxygen containing fluid at the set point pressure wherein when the pressure in the first stage outlet chamber is at the set point pressure, fluid flow communication between the first stage inlet chamber and the first stage outlet chamber is closed, and wherein when the pressure in the first stage outlet chamber is below the set point pressure, fluid flow communication between the first stage inlet and outlet chambers is present to raise the pressure in the first stage outlet chamber back to the set point pressure; and b) a second stage regulator means in fluid form communication with the first stage regulator means and disposed downstream thereof, the second stage regulator means comprising:

i) a second stage inlet chamber in fluid flow communication with the first stage outlet chamber;

ii) a second stage outlet chamber disposed downstream of the second stage inlet chamber and leading to a breathing apparatus for supplying the user's breathing requirements;

iii) a diaphragm means separating the second stage inlet chamber and the second stage outlet chamber wherein upon the occurrence of an inhalation event, the diaphragm means is in the open, flow position with the inhalation pressure transmitted to the second stage inlet chamber to thereby cause the pressure in the first stage outlet chamber to fall below the set point pressure so that fluid flow communication between the first stage inlet and outlet chambers is present to admit additional oxygen containing fluid into the first stage outlet chamber to thereby raise the pressure therein back to the set point pressure to close off communication between the first stage inlet chamber at the source pressure and the first stage outlet chamber at the set point pressure while fulfilling the user's breathing requirements; and c) a servo regulator means coupled to the second stage regulator means for regulating a pressure differential across the second stage inlet chamber and the second stage outlet chamber according to an altitude dependent breathing requirement and a G-force dependent breathing requirement wherein when the user's breathing requirements increase due to an increase in either the altitude above an altitude threshold or an increase in the G-force above a G-force threshold or both, the servo regulator means increases the pressure differential across the diaphragm means in response to the greater of the altitude dependent breathing requirement and the G-force dependent breathing requirement, respectively.

12. The oxygen breathing controller of claim 11 wherein the servo regulator means includes a manually operable release for releasing the oxygen containing fluid to flow to the user.

13. The oxygen breathing controller of claim 12 wherein the release means is a manually operable button.

14. The oxygen breathing controller of claim 12 wherein the servo regulator has a poppet, and wherein the release means opens the poppet to release the fluid flow.

15. The oxygen breathing controller of claim 11 further comprising means for controlling a minimum pressure limit with respect to altitude.

16. The oxygen breathing controller of claim 11 further comprising means for controlling a minimum pressure limit with respect to G-forces.

17. The oxygen breathing controller of claim 11 further comprising a G-force sensor means in fluid flow communication with the second stage regulator means and comprising a first G-sensor diaphragm means having a first effective area and a second G-sensor diaphragm means having a second effective area, the first and second effective areas having a predetermined ratio.

18. The oxygen breathing controller of claim 17 wherein the first G-sensor diaphragm means having the first effective area is exposed to a fluid flow between the G-sensor means and the servo regulator.

* * * * *